(12) United States Patent
Yang et al.

(10) Patent No.: US 11,464,765 B2
(45) Date of Patent: Oct. 11, 2022

(54) USE OF AN N-SUBSTITUTED PYRIDYL BENZISOSELAZOLONE COMPOUND

(71) Applicant: SHANGHAITECH UNIVERSITY, Shanghai (CN)

(72) Inventors: Haitao Yang, Shanghai (CN); Zhenming Jin, Shanghai (CN); Xiuna Yang, Shanghai (CN); Yao Zhao, Shanghai (CN); Zihe Rao, Shanghai (CN)

(73) Assignee: SHANGHAITECH UNIVERSITY, Shanghai (CN)

( * ) Notice: Subject to any disclaimer, the term of this patent is extended or adjusted under 35 U.S.C. 154(b) by 0 days.

(21) Appl. No.: 17/402,006

(22) Filed: Aug. 13, 2021

(65) Prior Publication Data

US 2021/0369696 A1 Dec. 2, 2021

Related U.S. Application Data

(63) Continuation of application No. PCT/CN2021/077481, filed on Feb. 23, 2021.

(30) Foreign Application Priority Data

Feb. 24, 2020 (WO) ................ PCT/CN2020/076375

(51) Int. Cl.
*A61K 31/41* (2006.01)
*A61K 31/4439* (2006.01)
*A61P 31/14* (2006.01)

(52) U.S. Cl.
CPC .......... *A61K 31/4439* (2013.01); *A61K 31/41* (2013.01); *A61P 31/14* (2018.01)

(58) Field of Classification Search
CPC ............................ A61K 31/41; A61K 31/4439
USPC .................................................. 514/359, 339
See application file for complete search history.

(56) References Cited

U.S. PATENT DOCUMENTS

2019/0161482 A1* 5/2019 Sucheck ................. A61P 35/00

FOREIGN PATENT DOCUMENTS

| CN | 1615883 A | 5/2004 |
|---|---|---|
| CN | 109475518 A | 3/2019 |
| CN | 111671762 A | 9/2020 |
| CN | 112110877 A | 12/2020 |

(Continued)

OTHER PUBLICATIONS

Holmes et al. "Coronaviridae: The viruses and their replication," Chapter 34, Fields Virology, vol. 1, pp. 1075-1076, Third Edition, 1995 (Year: 1995).*

(Continued)

*Primary Examiner* — Shengjun Wang
(74) *Attorney, Agent, or Firm* — Harness, Dickey & Pierce, P.L.C.

(57) ABSTRACT

Disclosed is a use of an N-substituted pyridyl benzisoselazolone compound. The use is particularly a use in the preparation of a medicament for treating and/or preventing a disease caused by coronavirus. The present disclosure surprisingly found that the N-substituted pyridyl benzisoselazolone compound, such as ebselen, can significantly inhibit the activity of the main protease of a coronavirus and the intracellular replication capability of SARS-CoV-2, which can be used for treating a disease caused by coronavirus.

4 Claims, 3 Drawing Sheets

(56) References Cited

FOREIGN PATENT DOCUMENTS

| | | |
|---|---|---|
| CN | 112645809 A | 4/2021 |
| WO | 2019133712 A1 | 7/2019 |

OTHER PUBLICATIONS

Consult QD , "Coronavirus have been around for centuries: What differentiates COVID-19?" May 2020, Padiatrics /News & Insights, (https://consultqd.clevelandclinic.org/coronaviruses-have-been-around-for-centuries-what-differentiates-2019-ncov/ (Year: 2019).*
Gioia et al. "Dynamic Docking: A paradigm shift in computational drug discovery," Molecules, 2017, vol. 22, 2029 (Year: 2017).*
Feb. 25, 2021 International Search Report issued in International Patent Application No. PCT/CN2021/077481.
Feb. 25, 2021 Written Opinion of the International Searching Authority issued in International Patent Application No. PCT/CN2021/077481.
Priority of PCT/CN2020/076375.
Zhenming Jin et al. "Structure of Mpro from SARS-CoV-2 and Discovery of its Inhibitors" Nature ,vol. 582, Jun. 11, 2020(Jun. 11, 2020), 289-293.
Van der Hoek, L., Pyre, K., Jebbink, M. et al. Identification of a new human coronavirus. Nat Med 2004,10, 368-373.
Stadler, K., Masignani, V., Eickmann, M. et al. SARS—beginning to understand a new virus. Nat Rev Microbiol 2003, 1, 209-218.
Ziebuhr, J. Molecular biology of severe acute respiratory syndrome coronavirus. Curr Opin Microbiol 2004, 7, 412-9.
De Wit, E., van Doremalen, N., Falzarano, D. et al. SARS and MERS: recent insights into emerging coronaviruses. Nat Rev Microbiol 2016,14, 523-534.
Akimkin V, Beer M, Blome S, et al. New Chimeric Porcine Coronavirus in Swine Feces, Germany, 2012. Emerg Infect Dis. 2016,22(7):1314-1315.
Ziebuhr, J.; Snijder, E. J.; Gorbalenya, A. E. Virus-encoded proteinases and proteolytic processing in the Nidovirales. J Gen Virol 2000, 81, 853-79.
Azad, G.K. & Tomar, R.SEbselen, a promising antioxidant drug: mechanisms of actionand targets of biological pathways. Mol Biol Rep 2014,41,4865.
Jonathan Kil, Edward Lobarinas, Christopher Spankovich, et.al. Safety and efficacy of ebselen for the prevention of noise-induced hearing loss: a randomised, double-blind, placebo-controlled, phase 2 trial. The Lancet 2017,390, 969-979.
Jeannette Guarner, MD, Three Emerging Coronaviruses in Two Decades: The Story of SARS, MERS, and Now COVID-19, American Journal of Clinical Pathology, , aqaa029.
Wang, M. et al. Remdesivir and chloroquine effectively inhibit the recently emerged novel coronavirus (2019-nCoV) in vitro. Cell Research, doi:10.1038/s41422-020-0282-0 (2020).

* cited by examiner

USE OF AN N-SUBSTITUTED PYRIDYL BENZISOSELAZOLONE COMPOUND

CROSS-REFERENCE TO RELATED APPLICATIONS

The present application is a continuation application of International Application No. PCT/CN2021/077481, filed on Feb. 23, 2021, which claims the priority of the International Application No. PCT/CN2020/076375 filed on Feb. 24, 2020. The entire disclosures of the above applications are incorporated herein by reference.

TECHNICAL FIELD

The present disclosure belongs to the field of biological medicament, particularly relates to a use of an N-substituted pyridyl benzisoselazolone compound.

BACKGROUND

Coronavirus is a type of virus that is closely related to humans and animals. Coronavirus HCoV-29E and HCoV-OC43 can cause common cold (van der Hoek, L., Pyrc, K., Jebbink, M. et al. *Identification of a new human coronavirus. Nat Med* 2004, 10, 368-373). Between 2002 and 2003, the severe acute respiratory syndrome (SARS) caused by SARS coronavirus resulted in 8098 infections and 774 deaths worldwide, with a fatality rate of 10% (Stadler, K., Masignani, V, Eickmann, M. et al. *SARS—beginning to understand a new virus. Nat Rev Microbiol* 2003, 1, 209-218). HCoV-NL63, identified in 2004, can also cause respiratory diseases similar to cold (van der Hoek, L., Pyrc, K., Jebbink, M. et al. *Identification of a new human coronavirus. Nat Med* 2004, 10, 368-373). Middle East respiratory syndrome coronavirus (MERS-CoV) appeared in 2012, and as of Apr. 26, 2016, it has caused 1728 infections with 624 deaths in 27 countries (de Wit, E., van Doremalen, N., Falzarano, D. et al. *SARS and MERS: recent insights into emerging coronaviruses. Nat Rev Microbiol* 2016, 14, 523-534.). The recently epidemic SARS-CoV-2 virus can cause COVID-19 with clinical manifestations of fever, dry cough and dyspnea, and the severe illnesses can be fetal (Jeannette Guarner, MD, *Three Emerging Coronaviruses in Two Decades: The Story of SARS, MERS, and Now COVID-19, American Journal of Clinical Pathology*, aqaa029). Coronavirus has a great impact on animal husbandry: porcine epidemic diarrhea virus (PEDV), gastroenteritis virus (transmissible gastroenteritis virus, TGEV) and porcine delta coronavirus (PDCoV, also known as delta virus), which can cause severe enteritis, diarrhea, vomiting and dehydration in pigs, causing huge loss to pig husbandry (Akimkin V, Beer M, Blome S, et al. *New Chimeric Porcine Coronavirus in Swine Feces, Germany, 2012. Emerg Infect Dis.* 2016, 22(7):1314-1315). Feline infectious peritonitis virus (FIPV) can cause a fatal disease in cats. Avian infectious bronchitis virus (IBV) that infects poultry is a widespread poultry disease, which has a huge economic impact on poultry industry.

Coronavirus belongs to the Orthocoronavirinae subfamily of the Coronaviridae family, Nidovirales order in taxonomy. The genome sequence of SARS-CoV-2 coronavirus has been published recently, which has about 90% similarity with the nucleotide sequence of SARS-CoV, and about 80% sequence similarity with SARS-CoV in protein sequence. The genome of coronavirus is a single-stranded positive-sense RNA with a length of approximately 28 kb, encoding mainly structural proteins required for virus packaging and non-structural proteins associated with replication and transcription. The development of drugs and vaccines for the treatment of coronavirus-associated diseases mainly targets the above two types of proteins. Two-thirds of the genes in the viral genome encodes mainly non-structural proteins. The virus encodes two polymerase proteins, pp1a and pp1ab, which are involves in the replication process of the virus. Proteins pp1a and pp1ab can be cleaved into 16 non-structural proteins nsp1-16 by papain-like protease and main protease encoded by the virus. Only when these functional subunits are cleaved into independent protein units by proteases encoded by the virus can the virus complete normal functions of transcription and replication, and then assemble into a replication and transcription complex, thus completing the replication and transcription of the virus. Among them, papain-like protease has 3 restriction sites, while the main protease has 11 restriction sites on pp1a and pp1ab. It is evident that the main protease plays a key regulatory role in the processes of transcription and replication of the virus, so it has become the focus of research (Ziebuhr, J.; Snijder, E. J.; Gorbalenya, A. E. *Virus-encoded proteinases and proteolytic processing in the Nidovirales. J Gen Virol* 2000, 81, 853-79; Ziebuhr, J. *Molecular biology of severe acute respiratory syndrome coronavirus. Curr Opin Microbiol* 2004, 7, 412-9). Due to the importance of the main protease for the proliferation and replication of coronaviruses, it is particularly important for drug development to find inhibitors with high safety profile and strong specificity for the catalytic sites of the main protease.

Ebselen belongs to N-substituted pyridyl benzisoselazolidone compound, which is an organic selenium compound. It can be used as a glutathione peroxidase regulator or analog compound with good antioxidant function due to its special function similar to glutathione peroxidase. Ebselen is a multifunctional compound that can protect important intracellular components from oxidative damage. It has been found that ebselen can inhibit many enzymes involved in various biological processes, including zinc finger protein, lipoxygenase, nitric oxide synthase, NADPH oxidase, H+-K+-ATPase, horseradish peroxidase, glutamate dehydrogenase and lactate dehydrogenase, etc. (Azad, G. K. & Tomar, R. S *Ebselen, a promising antioxidant drug: mechanisms of action and targets of biological pathways. Mol Biol Rep* 2014, 41, 4865). The molecular formula of ebselen is as follows:

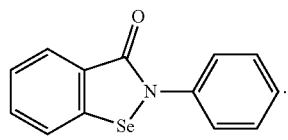 [SMILES: O=c1c2ccccc2[se]n1-c1ccccc1]

Ebselen can affect a variety of intracellular biological reaction processes. It can not only act as a scavenger of active oxygen and free radicals, thereby exerting anti-oxidative stress, inhibiting cell apoptosis, and maintaining genomic stability; but also can affect the immune system, regulate the host's immune system and response to various stimuli, exhibiting anti-inflammatory effects (Azad, G. K. & Tomar, R. S *Ebselen, a promising antioxidant drug: mechanisms of action and targets of biological pathways. Mol Biol Rep* 2014, 41, 4865).

Ebselen shows good anti-inflammatory activity in a variety of inflammation models without the gastrointestinal stimulating effect of non-steroidal anti-inflammatory drugs.

It can be used clinically to treat Meniere's disease, endolymphedema, rheumatoid arthritis, and osteoarthritis, etc. (Azad, G. K. & Tomar, R. S *Ebselen, a promising antioxidant drug: mechanisms of actionand targets of biological pathways. Mol Biol Rep* 2014, 41, 4865; Jonathan Kil, Edward Lobarinas, Christopher Spankovich, et. al. *Safety and efficacy of ebselen for the prevention of noise-induced hearing loss: a randomised, double-blind, placebo-controlled, phase 2 trial. The Lancet* 2017,390, 969-979; J. Kil, Treatment ofMeniere's Disease; Chinese Patent: CN109475518A, 2019 Mar. 15). A large amount of oral administration of ebselen can cause acute toxicity: the oral lethal dose in rats is >4600 mg/kg, and the oral lethal dose in mice is >2150 mg/kg. In a patent on the treatment of Meniere's disease in 2019, Sound Pharmaceuticals Inc conducted a phase II clinical trial of ebselen for the treatment of Meniere's disease, and the results showed that ebselen is safe and well tolerated, with no obvious toxic reaction and side effects observed and a few mild headache symptoms that recovered soon after discontinuing medication (Jeannette Guarner; MD, *Three Emerging Coronaviruses in Two Decades: The Story of SARS, MERS, and Now COVID-19, American Journal of Clinical Pathology*, aqaa029; Akimkin V Beer M, Blome S, et al. *New Chimeric Porcine Coronavirus in Swine Feces*, Germany, 2012. *Emerg Infect Dis.* 2016, 22(7):1314-1315). Clinical trials have confirmed the high safety profile of ebselen.

There is a record in the prior art (CN 1615883A) that ebselen inhibits HBV virus and treats HBV virus-associated diseases. However, ebselen in this patent mainly plays a role in immune regulation, which is not related to the role of the main protease, the replication and protein synthesis of a virus, and ebselen is used in combination with other drugs. So far, it has not been found that ebselen can be used to treat coronavirus-associated diseases.

SUMMARY

The technical problem to be solved in the present disclosure is to provide a use, particularly a use in the preparation of a medicament for treating diseases caused by coronavirus, of an N-substituted pyridyl benzisoselazolone compound aiming at the deficiency that there is no effective medicament for treating and/or preventing the diseases caused by coronavirus.

The present disclosure solves the above-mentioned technical problems mainly by the following technical solutions.

The first aspect of the present disclosure is to provide a use of an N-substituted pyridyl benzisoselazolone compound in the preparation of a medicament for treating and/or preventing diseases caused by coronavirus, wherein the N-substituted pyridyl benzisoselazolone compound is represented by general formula I as follows:

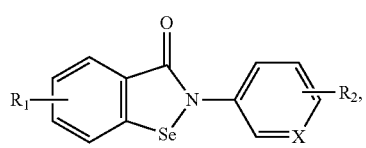

in the general formula I, $R_1$ is selected from hydrogen, halogen, linear or branched $C_1$-$C_4$ alkyl group or alkoxy; and $R_1$ is substituted at 3-, 4-, 5- or 6-position;

$R_2$ is selected from hydrogen, halogen, linear or branched $C_1$-$C_4$ alkyl group or alkoxy; and $R_2$ is substituted at any carbon atom on 2-pyridine ring;

X represents a nitrogen atom with a substitution position at 2-, 3- or 4-position.

The N-substituted pyridyl benzisoselazolone compound is a compound represented by general formula (Ia) as follows:

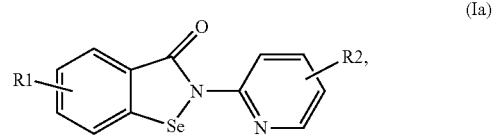

or
wherein $R^1$ and $R^2$ are defined as above;
a compound represented by general formula (Ib):

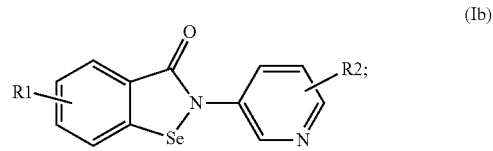

R1 and R2 are defined as above; and a compound represented by general formula (Ic):

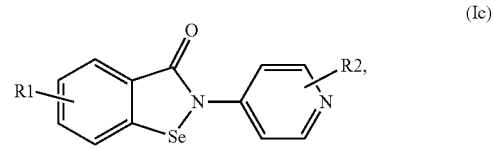

wherein R1 and R2 are defined as above.

The N-substituted pyridyl benzisoselazolone compound more preferably is ebselen represented by the formula as follows:

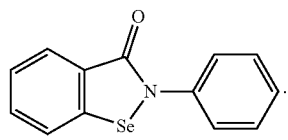 [SMILES: O=c1c2ccccc2[se]n1-c1ccccc1]

Preferably, the disease is a mammal disease or an avian disease.

Preferably, the mammal comprises human, swine and feline.

Coronavirus described in the present disclosure, which is defined as known in the art, belongs to the Orthocoronavirinae subfamily of the Coronaviridae family, Nidovirales order in taxonomy. Coronavirus is a large group of naturally occurring RNA virus with an envelope and single-strand positive-sense genome.

The aim of the present disclosure is to provide a potential therapy regimen for the disease caused by coronavirus infection. The coronavirus described in the present disclosure preferably belongs to Orthocoronavirinae subfamily, more preferably belong to Alpha Coronavirus genus, Beta Coronavirus genus, Gamma Coronavirus genus or Delta Coronavirus genus.

In a preferred embodiment of the present disclosure, the N-substituted pyridyl benzisoselazolone compound, such as ebselen, can be used not only to treat a disease caused by SARS-CoV-2 (Beta Coronavirus genus), but also to treat a major infectious disease caused by other coronaviruses such as SARS-CoV (Beta Coronavirus genus) and MERS-CoV. Moreover, the compound can be used as a common cold medicine in treating a disease caused by coronaviruses such as HCoV-HKU1 (Human coronavirus HKU1; Beta Coronavirus genus), HCoV-NL63 (Human coronavirus NL63; Alpha Coronavirus genus), HCoV-OC43 (Human coronavirus OC43) or HCoV-229E (Human coronavirus 229E; Alpha Coronavirus genus), etc.; or, the compound can be used as a veterinary medicine in treating an animal disease caused by virus such as porcine transmissible gastroenteritis virus (TGEV; Alpha Coronavirus genus), porcine epidemic diarrhea virus (PEDV; Alpha Coronavirus genus), porcine delta coronavirus (PDCoV; Delta Coronavirus genus), feline infectious peritonitis virus (FIPV; Alpha Coronavirus genus), or avian infectious bronchitis virus (IBV; Gamma Coronavirus genus), etc.

Therefore, the coronavirus in the present disclosure is preferably selected from SARS-CoV-2, SARS-CoV, MERS-CoV, HCoV-HKU1, HCoV-NL63, HCoV-OC43, HCoV-229E, TGEV, PEDV, PDCoV, FIPV or IBV.

Prior to supplying for clinical use, any medicament must be prepared in a form suitable for medical and preventive applications, which is called the dosage form of a medicament, or medicament for short. After the medicament is prepared in different dosage forms, it is convenient and easy to accept for patients, which not only makes the dosage of the medicament accurate, but also improves the stability of the medicament, sometimes this can also reduce the toxic and side effects. Besides, it is also convenient for storage, transportation and carrying of the medicament. There are dozens of dosage forms, among which 20 to 30 more are more commonly used, such as oral dosage form and injection dosage.

In the present disclosure, the medicament is preferably in an oral dosage form.

The second aspect of the present disclosure is to provide a method for treating a disease caused by coronavirus using an N-substituted pyridyl benzisoselazolone compound or a pharmaceutical composition comprising the same, the N-substituted pyridyl benzisoselazolone compound is represented by formula I as follows:

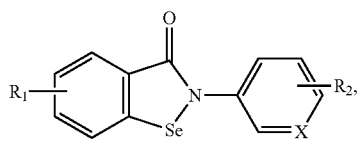

(I)

wherein in the general formula I, $R_1$ is selected from hydrogen, halogen, linear or branched $C_1$-$C_4$ alkyl group or alkoxy; and R1 is substituted at 3-, 4-, 5- or 6-position;

$R_2$ is selected from hydrogen, halogen, linear or branched $C_1$-$C_4$ alkyl group or alkoxy; and $R_2$ is substituted at any carbon atom on 2-pyridine ring;

X represents a nitrogen atom, the substitution position thereof is 2-, 3- or 4-.

The N-substituted pyridyl benzisoselazolone compound preferably comprises a compound represented by general formula (Ia) as follows:

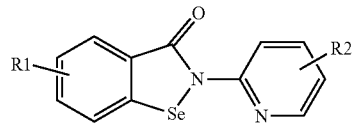

(Ia)

wherein R1 and R2 are defined as above;
a compound represented by general formula (Ib):

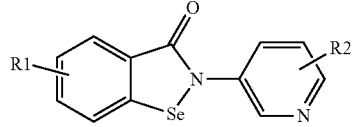

(Ib)

R1 and R2 are defined as above; and a compound represented by general formula (Ic):

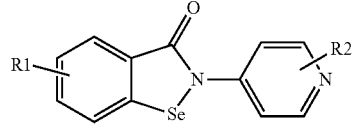

(Ic)

wherein R1 and R2 are defined as above.

The N-substituted pyridyl benzisoselazolone compound is ebselen represented by the formula as follows:

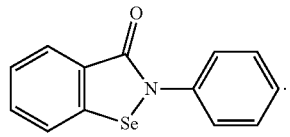

Wherein, the formulation of the pharmaceutical composition is preferably oral formulation.

The third aspect of the present disclosure is to provide a method for treating a disease caused by coronavirus in an animal suffering from a disease caused by coronavirus, comprising: administering an effective amount of N-substituted pyridyl benzisoselazolone compounds or a pharmaceutical composition comprising the same to the animal, the N-substituted pyridyl benzisoselazolone compound is represented by general formula I as follows:

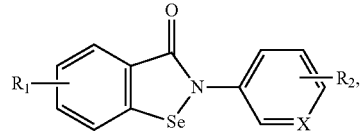

(I)

$R_1$ in the general formula I is selected from hydrogen, halogen, linear or branched $C_1$-$C_4$ alkyl group or alkoxy; $R_2$ is substituted at any carbon atom on 2-pyridine ring;

$R_2$ is selected from hydrogen, halogen, linear or branched $C_1$-$C_4$ alkyl group or alkoxy; $R_2$ is substituted at any carbon atom on 2-pyridine ring;

X represents a nitrogen atom with a substitution position at 2-, 3- or 4-.

The N-substituted pyridyl benzisoselazolone compound preferably comprises a compound represented by general formula (Ia) as follows:

(Ia)

wherein R1 and R2 are defined as above;
a compound represented by general formula (Ib):

(Ib)

R1 and R2 are defined as above; a compound represented by general formula (Ic):

(Ic)

wherein R1 and R2 are defined as above.

The N-substituted pyridyl benzisoselazolone compound is ebselen represented by the formula as follows:

The animal is preferably an animal capable of developing a disease caused by coronavirus, such as a mammal and an avian. The mammal in the present disclosure preferably comprises human, swine and feline.

The specific definitions for the coronavirus, the N-substituted pyridyl benzisoselazolone compound and the diseases described in the second and third aspects in the present disclosure are the same as those for coronavirus, the N-substituted pyridyl benzisoselazolone compound and the diseases in the first aspect described above.

The present disclosure finds that ebselen can be used for treating diseases caused by coronavirus, through in vitro enzyme activity assays and in vitro cell-virus assays.

The positive and progressive effects of the present disclosure are:

The present disclosure finds that an N-substituted pyridyl benzisoselazolone compound, such as ebselen, can be used for treating diseases caused by coronavirus through in vitro enzyme activity assays and in vitro cell-virus assays. There is no specific medicament for human coronavirus that has been approved for marketing, and the ebselen therapy regimen has low toxic and side effects, and is easy to implement for oral administration, which can fill the gaps of the prior art.

DETAILED DESCRIPTION

Example 1

Figure 1:
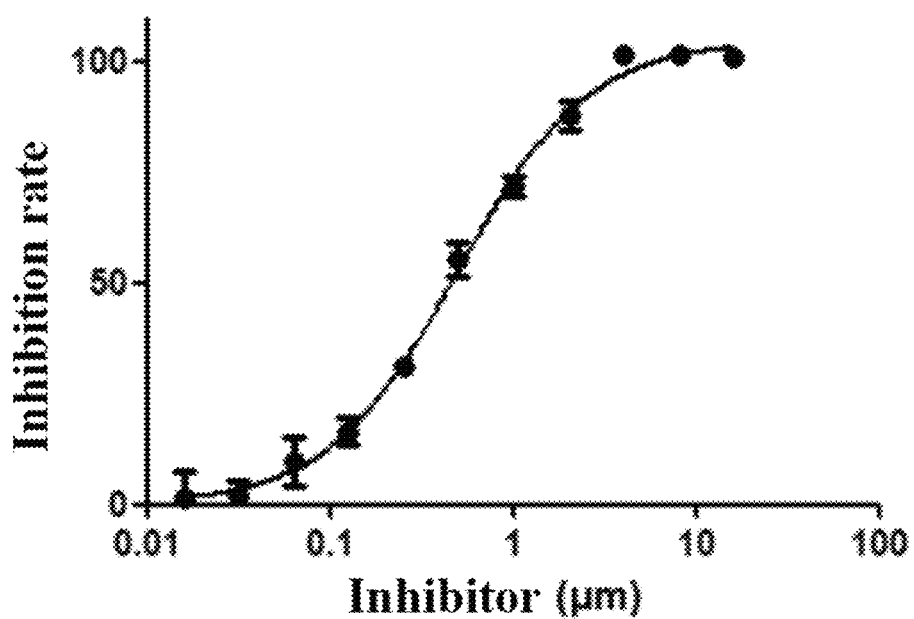
FIG. 1 shows that ebselen has a strong inhibition activity on the main protease of novel coronavirus (SARS-CoV-2).
Figure 2:
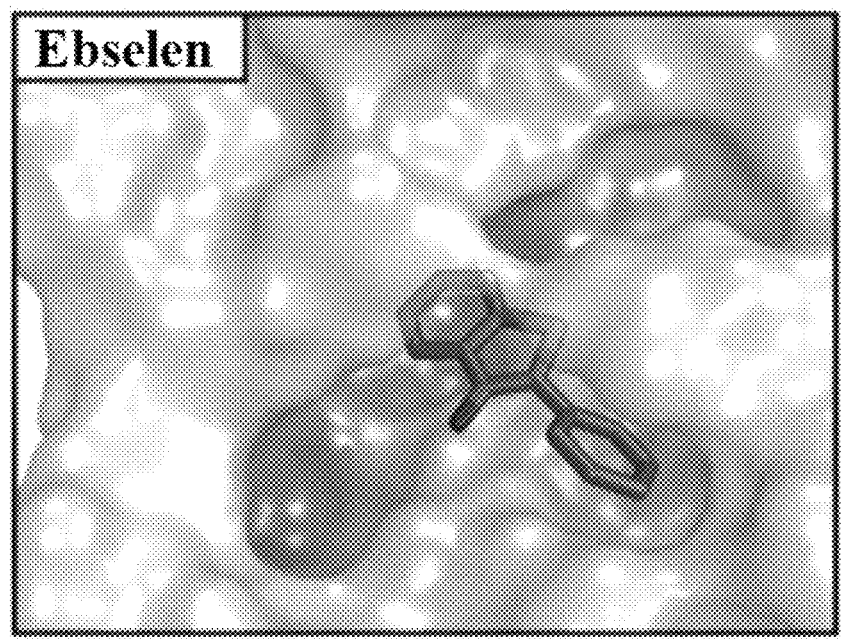
FIG. 2 shows that ebselen is an inhibitor targeting the activity pocket of the main protease of novel coronavirus by molecular docking.

It can be seen from in vitro enzyme activity assays that ebselen can significantly inhibit the activity of the main protease of novel coronavirus (SARS-CoV-2), with an $IC_{50}$ value of 0.48 μM (FIG. 1). Molecular docking shows that ebselen is an inhibitor targeting the active pocket of the main protease of novel coronavirus (FIG. 2).

Figure 3:
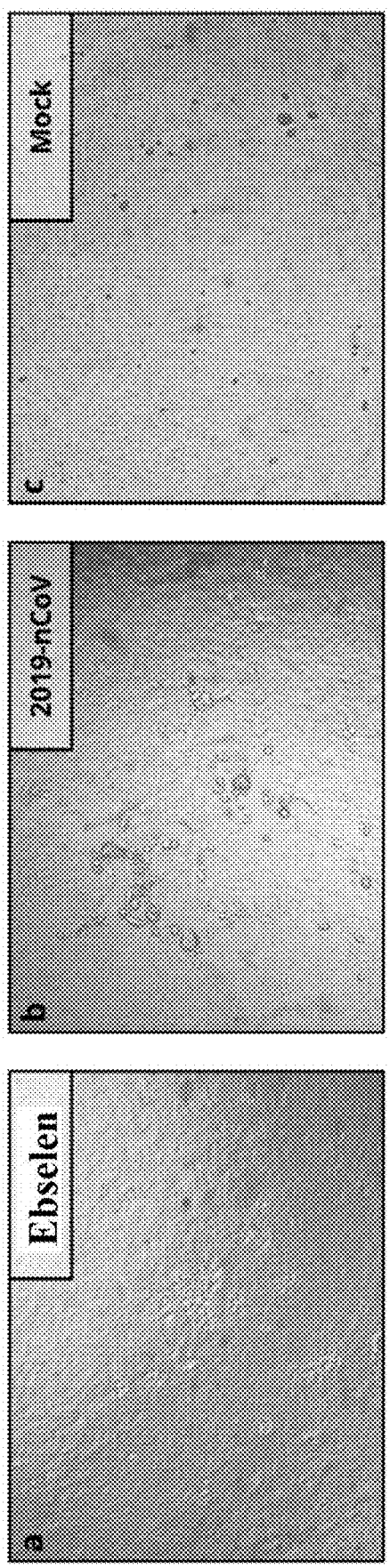
FIG. 3 showing that ebselen can prevent cytopathy caused by novel coronavirus infection (a: ebselen addition, b: cells infected with novel coronavirus, c: Mock control, added with 0.1% DMSO).
Figure 4:
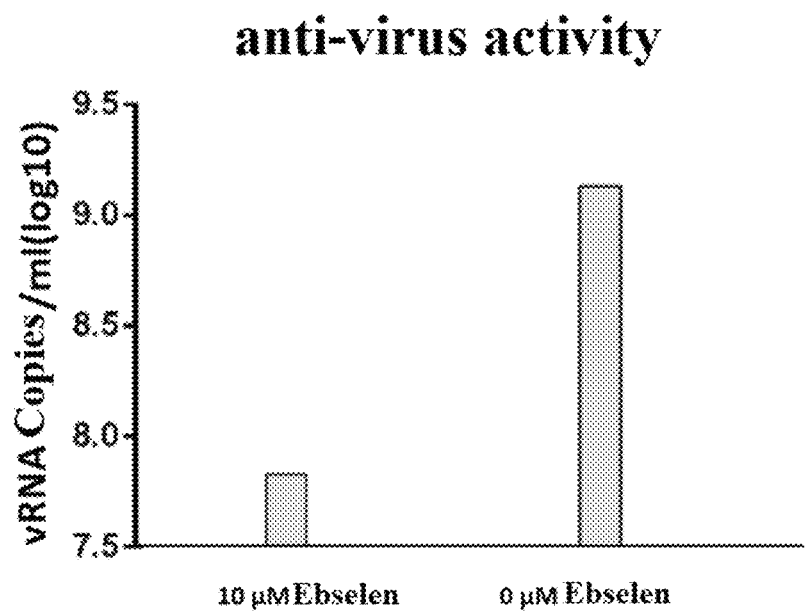
FIG. 4 shows the antiviral assay at cell level.

It can be seen from in vitro cell-virus assays that ebselen can prevent cytopathy caused by novel coronavirus infection (FIG. 3), and significantly inhibits the replication ability of SARS-CoV-2 in cells (FIG. 4). Meanwhile, clinical trials have confirmed that ebselen has high safety profile and can therefore be used for the treatment of diseases caused by coronavirus.

See Wang, M. et al. Remdesivir and chloroquine effectively inhibit the recently emerged novel coronavirus (2019-nCoV) in vitro. *Cell Research*, doi: 10.1038/s41422-020-0282-0 (2020) for the detailed experimental methods of in vitro enzyme activity assays and in vitro cell-virus assays.

Figure 5:
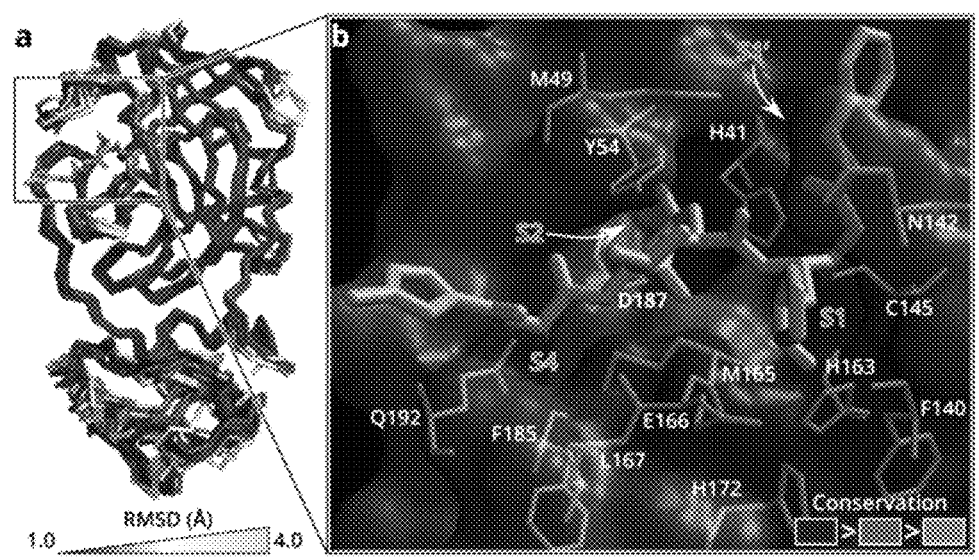
FIG. 5 shows the superimposed structure of the main proteases from different species of coronavirus; indicating that the binding pocket for substrate/inhibitor (bold) is very conservative (12 structures of coronavirus including SARS-CoV-2, SARS-CoV, MERS-CoV, HCoV-HKU1, BtCoV-HKU1, MHV-A59, PEDV, FIPV, TGEV, HCoV-NL63, HCoV-229E and IBV are aligned).

Since the substrate binding pocket of coronavirus main protease is highly conserved (FIG. 5), inhibitors (ebselen, etc.) targeting its binding pocket will have a broad-spectrum anti-coronavirus effect. It can be seen that the ebselen of the present disclosure can be used to treat a disease caused by SARS-CoV-2, and should also be able to treat a major infectious disease caused by other coronaviruses such as SARS-CoV and MERS-CoV. It can also be used as a common cold medicine for treating a disease caused by coronavirus such as HCoV-HKU1, HCoV-NL63, HCoV-OC43 and HCoV-229E; in addition, it can also be used as a veterinary medicine to treat an animal disease caused by porcine transmissible gastroenteritis virus (TGEV), porcine epidemic diarrhea virus (PEDV), porcine delta coronavirus (PDCoV), feline infectious peritonitis virus (FIPV), avian infectious bronchitis virus (IBV) or other animal diseases.

Although the specific embodiments of the present disclosure are described above, those skilled in the art should understand that the embodiments are merely illustrative examples, and various modifications and variations can be made to those embodiments without departing from the spirit or scope of the present disclosure. Thus, the protection scope of the present disclosure is defined by the appended claims.

What is claimed is:

1. A method for treating a disease caused by coronavirus in an animal suffering from coronavirus infection, comprising: administering an effective amount of an N-substituted benzisoselazolone compound or a pharmaceutical composition comprising the same to the animal, wherein the N-substituted benzisoselazolone compound is represented by general formula I as follows:

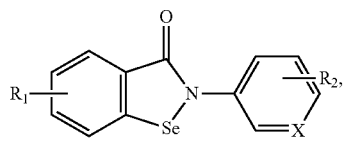

(I)

wherein in the general formula I, $R_1$ is selected from hydrogen, halogen, linear or branched $C_1$-$C_4$ alkyl group or alkoxy; and $R_1$ is substituted at 3-, 4-, 5- or 6-position;

$R_2$ is selected from hydrogen, halogen, linear or branched $C_1$-$C_4$ alkyl group or alkoxy;

X represents a carbon atom; and wherein the coronavirus is SARS-CoV-2, SARS-CoV, MERS-CoV, HCoV-HKU1, HCoV-NL63, HCoV-OC43, HCoV-229E, PDCoV, FIPV or IBV.

2. The method of claim 1, wherein the animal is a mammal or an avian;

or, the pharmaceutical composition is in an oral dosage form;

or, the pharmaceutical composition is a cold medicine or a veterinary medicine.

3. The method of claim 1, wherein the N-substituted pyridyl benzisoselazolone compound is a represented by the formula as follows:

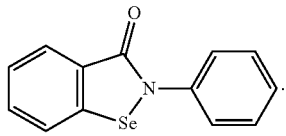 [SMILES: O=c1c2ccccc2[se]n1-c1ccccc1]

4. The method of claim 2, wherein the mammal comprises human, swine and feline.

* * * * *